United States Patent [19]

Aoki et al.

[11] 4,336,325
[45] Jun. 22, 1982

[54] COLOR PHOTOGRAPHIC LIGHT-SENSITIVE ELEMENT

[75] Inventors: Kozo Aoki; Satoru Sawada; Nobuo Furutachi, all of Minami-ashigara, Japan

[73] Assignee: Fuji Photo Film Co., Ltd., Kanagawa, Japan

[21] Appl. No.: 199,125

[22] Filed: Oct. 22, 1980

[30] Foreign Application Priority Data

Oct. 23, 1979 [JP] Japan ................... 54-136730

[51] Int. Cl.³ .............................................. G03C 1/40
[52] U.S. Cl. .................................. 430/505; 430/554; 430/555; 430/558
[58] Field of Search ............... 430/554, 555, 505, 386, 430/387, 558

[56] References Cited

U.S. PATENT DOCUMENTS 3,935,015  1/1976  Arai et al. ........................... 430/554
4,243,747  1/1981  Nakamura et al. ................. 430/554

FOREIGN PATENT DOCUMENTS 2546023  4/1976  Fed. Rep. of Germany ...... 430/554

*Primary Examiner*—J. Travis Brown
*Attorney, Agent, or Firm*—Sughrue, Mion, Zinn, Macpeak and Seas

[57] ABSTRACT

A color photographic light-sensitive element comprising a support having thereon a silver halide emulsion layer containing therein a 3-anilino-5-pyrazolone magenta-color-forming coupler represented by the following general formula (I):

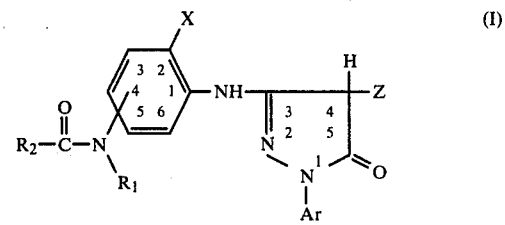

wherein

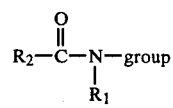

(an N-substituted acylamino group) is present at the 4- or 5-position of the anilino group; $R_1$ represents a substituted or unsubstituted alkyl group, an alkenyl group, a cycloalkyl group, a cycloalkyl, a cycloalkenyl group or an aralkyl group; $R_2$ represents an aliphatic hydrocarbon group, a heterocyclic group or an aryl group; X represents a halogen atom or an alkoxy group; Z represents hydrogen or a coupling-off group; and Ar represents an aryl group.

The 3-anilino-5-pyrazolone magenta-color-forming coupler is useful in preventing the formation of yellow stain due to light irradiation in unexposed areas of a color photographic light-sensitive element after color development processing.

17 Claims, No Drawings

COLOR PHOTOGRAPHIC LIGHT-SENSITIVE ELEMENT

BACKGROUND OF THE INVENTION

The present invention relates to a silver halide photographic light-sensitive element containing a novel magenta-color-forming coupler.

After exposing a color silver halide photographic light-sensitive element to light, the element is typically developed with an aromatic primary amine developing agent. The developing agent is oxidized during development and reacts with a coupler to form a dye, with a color image thus being formed. In this system, a subtractive method is generally used for color reproduction, in which blue, green and red colors are reproduced by forming yellow, magenta and cyan color images which are in complementary relation thereto, respectively. In general, acylacetamide of dibenzoylmethane type couplers are employed for forming yellow color images; pyrazolone, cyanoacetyl, or indazolone type couplers are used for forming magenta color images; and phenol type couplers, for example, phenols and naphthols, are utilized for forming cyan color images.

To produce color photographs, couplers which form dyes in a developer or in a light-sensitive photographic emulsion layer(s).

A variety of 5-pyrazolone type couplers for forming magenta color images are known. Known substituents at the 3-position of the 5-pyrazolone ring include alkyl groups, aryl groups, alkoxy groups, as described in U.S. Pat. No. 2,439,098, acylamino groups, as described in U.S. Pat. Nos. 2,369,489 and 2,600,788, ureido groups, as described in U.S. Pat. No. 3,558,319, and anilino groups. 3-Anilino-5-pyrazolone type couplers have often been described in the art since U.S. Pat. No. 2,311,081 (U.S. Pat. No. Re. 22,329) was issued and several improvements therein have been proposed. British Pat. No. 956,261 discloses that azomethine dyes obtained from derivatives in which the ortho position of the anilino group is substituted with an alkoxy group or a halogen atom have advantageous spectral absorption properties for color photography, in that undesired absorption in the red light region is particularly low.

Specific examples of diffusion resistant couplers of this type and are capable of being incorporated into photographic emulsions are described, for example, in U.S. Pat. Nos. 3,684,514, 3,930,861, 3,907,571, 3,928,044, 3,926,634 and 3,935,015, and Japanese Patent Application (OPI) No. 123033/74 (the term "OPI" as used herein refers to a "published unexamined Japanese patent application"). For example, the couplers described in U.S. Pat. No. 3,935,015 are 3-(acylaminoanilino)-5-pyrazolones represented by the formula (M) and are well known:

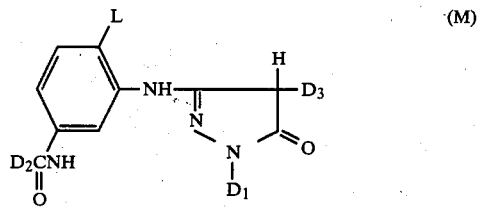

(M)

wherein $D_1$ represents an aryl group or a heterocyclic group, $D_2$ represents a straight chain, branched chain or cyclic alkyl group having 7 to 23 carbon atoms, $D_3$ represents a coupling-off group (defined hereinafter), and L represents a halogen atom or an alkoxy group having 1 to 18 carbon atoms.

These couplers have the characteristics that the undesired absorption of magenta azomethine dyes obtained upon color formation using the same in the red light region is low, the cut-off of the main absorption is good at the longer wavelength side, and magenta color images having a high color density are obtained because the coupling speed is high. Furthermore, the solubility in organic solvents having a high boiling point is improved, so that, after dissolving these couplers in organic solvents, the couplers can be emulsion-dispersed in an aqueous medium in the form of fine colloidal particles and then added to emulsions.

However, these couplers have the disadvantages that the degree of yellow staining at the unexposed portion after color development processing is high, and this degree of yellow staining increases upon light irradiation. They have the further disadvantages that color fading of the magenta color images obtained upon color development using these compounds occurs to a significant degree upon irradiation with light, and the color balance required for color photography is damaged by exposure to light, since, for example, in a color film or a color paper, particularly in a color paper, the color images are formed when three colors such as yellow, magenta and cyan combine with each other, but among these colors, the magenta color is not faster than any other color upon light irradiation. These disadvantages become fatal defects for color light-sensitive elements, such as color printing papers and the like. Thus, improved couplers which do not have these disadvantages have been strongly desired.

SUMMARY OF THE INVENTION

A first object of the present invention is to provide a coupler with which the formation of yellow stain at the unexposed areas of a color photographic light-sensitive element after color development processing is minimized, i.e., with which yellow stain does not occur initially nor does a yellow stain occur later upon irradiation of the dye image with light.

A second object of the present invention is to provide a coupler having the property that color images formed therefrom are resistant to fading even if the magenta color images obtained after color development are irradiated with light.

A third object of the present invention is to provide a light-sensitive element which is suitable for simple development processing without stabilizing processing with formaldehyde or the like being required.

A fourth object of the present invention is to provide a novel coupler which has a high color formation rate and provides magenta color images having high density.

A fifth object of the present invention is to provide a coupler which has excellent solubility in an organic solvent and is suitable for use in a method which comprises emulsion-dispersing the coupler in an aqueous medium in the form of fine colloidal particles, and then incorporating the dispersion into an emulsion.

These and other objects of the present invention will become more apparent from the detailed description of the invention and the examples given hereinbelow.

These objects are effectively achieved by a color photographic light-sensitive element containing in a silver halide photographic emulsion layer(s) thereof, as a magenta color image-forming coupler, a 3-anilino-5-pyrazolone coupler wherein the anilino group thereof is substituted with a halogen atom or an alkoxy group at the 2-position of the anilino group, and with the

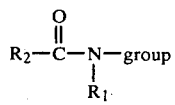

(an N-substituted acylamino group) at the 4- or 5-position of the anilino group. Furthermore, the coupler has an aryl group present at the 1-position of the pyrazolone nucleus. Still further, the 4-position of the pyrazolone nucleus may also be a hydrogen atom, or may be substituted with a coupling off group.

DETAILED DESCRIPTION OF THE INVENTION

The term "coupling-off group" as used herein has the same meaning as when generally used in the color-forming coupler field, and refers to a group other than hydrogen which is eliminated by the oxidation product of an aromatic primary amine developing agent during the coupling reaction.

Couplers which are useful for the present invention comprise compounds represented by formula (I)

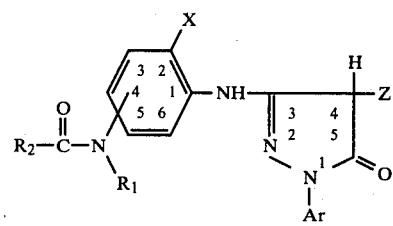

wherein the

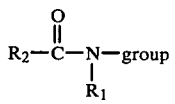

(an N-substituted acylamino group) is present at the 4- or 5-position of the anilino group; $R_1$ represents a substituted or unsubstituted alkyl group, an alkenyl group, a cycloalkyl group, a cycloalkenyl group or an aralkyl group; $R_2$ represents an aliphatic hydrocarbon group, a heterocyclic group or an aryl group; X represents a halogen atom or an alkoxy group; Z represents hydrogen or a coupling-off group; and Ar represents an aryl group.

$R_1$, $R_2$, X, Z and Ar in formula (I) above are described in more detail below.

In formula (I), $R_1$ preferably represents a straight chain or branched chain alkyl group having 1 to 22 carbon atoms (for example, a methyl group, an ethyl group, a butyl group, a heptyl group, a tetradecyl group, a hexadecyl group, an octadecyl group, a dodecyl group, etc.), an alkenyl group having 2 to 22 carbon atoms (for example, an allyl group, etc.), a cycloalkyl group having 5 to 22 carbon atoms including a cross-linked type cyclic hydrocarbon group (for example, a cyclopentyl group, a cyclohexyl group, a norbornyl group, etc.), an aralkyl group having 7 to 22 carbon atoms (for example, a benzyl group, a phenethyl group, etc.) or a cycloalkenyl group having 5 to 22 carbon atoms (for example, a cyclopentenyl group, a cyclohexenyl group, etc.). These groups can be substituted with one or more substituents selected from a halogen atom, a nitro group, a cyano group, an aryl group (for example, a phenyl group, a naphthyl group, etc.), an alkoxy group (for example, a methoxy group, an ethoxy group, etc.), an aryloxy group (for example, a phenyloxy group, a naphthyloxy group, etc.), a carboxy group, an alkylcarbonyl group (for example, an acetyl group, a tetradecanoyl group, etc.), an arylcarbonyl group (for example, a benzoyl group, etc.), an alkoxycarbonyl group (for example, a methoxycarbonyl group, a benzyloxycarbonyl group, etc.), an aryloxycarbonyl group (for example, a phenyloxycarbonyl group, a p-tolyloxycarbonyl group, etc.), an acyloxy group (for example, an acetyloxy group, a tetradecanoyloxy group, etc.), a sulfamoyl group (for example, an N-ethylsulfamoyl group, an N-octadecylsulfamoyl group, etc.), a carbamoyl group (for example, an N-ethylcarbamoyl group, an N-methyl-N-dodecylcarbamoyl group, etc.), an acylamino group (for example, an acetylamino group, a benzamido group, etc.), a diacylamino group (for example, a succinimido group, a hydantoinyl group, etc.), a ureido group (for example, a methylureido group, a phenylureido group, a (4-methoxyphenyl)ureido group, etc.), an N-alkylanilino group (for example, an N-methylanilino group, an N-butylanilino group, etc.), an N-acylanilino group (for example, an N-acetylanilino group, an N-trichloroacetylanilino group, etc.), a hydroxy group, and a mercapto group. Where $R_1$ is an alkyl group substituted with a fluorine atom, $R_1$ can also be a so-called polyfluoroalkyl group.

In formula (I), $R_2$ preferably represents an aliphatic hydrocarbon group, and more preferably an alkyl group having 1 to 32 carbon atoms (for example, a methyl group, an ethyl group, a butyl group, a heptyl group, a dodecyl group, a tetradecyl group, a hexadecyl group, an octadecyl group, etc.), an alkenyl group having 2 to 32 carbon atoms (for example, an allyl group, etc.), a cycloalkyl group having 5 to 32 carbon atoms (including a cross-linkage type cyclic hydrocarbon group, for example, a cyclophenyl group, a cyclohexyl group, a norbornyl group, etc.), an aralkyl group having 7 to 32 carbon atoms (for example, a benzyl group, a phenethyl group, etc.) or a cycloalkenyl group having 5 to 32 carbon atoms (for example, a cyclopentenyl group, a cyclohexenyl group, etc.). These groups can be substituted with one or more of the substituents as described above as the substituent groups for $R_1$.

Furthermore, $R_2$ can represent an aryl group (for example, a phenyl group, an α- or β-naphthyl group, etc.) which may be substituted with one or more substituents. Suitable substituents include the same substituents as described above as the substituent groups for $R_1$.

Furthermore, $R_2$ can represent a heterocyclic group (for example, a 5-membered or 6-membered heterocyclic ring or condensed heterocyclic ring group containing at least one hetero atom selected from a nitrogen atom, an oxygen atom, and a sulfur atom. Examples include a pyridyl group, a quinolyl group, a furyl group, a benzothiazolyl group, an oxazolyl group, an imidazolyl group, a naphthoxazolyl group, or a heterocyclic group substituted with one or more of the substituents as described above as the substituent groups for $R_1$.

In formula (I), X represents a halogen atom (for example, a chlorine atom, a bromine atom, etc.) or an alkoxy group having 1 to 22 carbon atoms (for example, a methoxy group, an ethoxy group, a heptoxy group, a tetradecyloxy group, a hexadecyloxy group, an octadecyloxy group, an allyloxy group, a benzyloxy group, a phenethyloxy group, etc.). The alkoxy group can be substituted with one or more substituents selected from a halogen atom, a nitro group, a cyano group, an alkoxy group (for example, a methoxy group, an ethoxy group, etc.), an aryloxy group (for example, a phenyloxy group, a naphthyloxy group, etc.), an alkylcarbonyl group (for example, an acetyl group, a tetradecanoyl group, etc.), an alkoxycarbonyl group (for example, a methoxycarbonyl group, a benzyloxycarbonyl group, etc.), an acylamino group (for example, an acetylamino group, a benzamido group, etc.), a sulfonamido group (for example, a methanesulfonamido group, a p-toluenesulfonamido group, etc.), a hydroxy group and a mercapto group. Where X is an alkoxy group substituted with a fluorine atom, X can also be a so-called polyfluoroalkoxy group.

In formula (I), Z can represent hydrogen or a coupling-off group. Suitable coupling-off groups represented by Z include, for instance, a thiocyano group, an acyloxy group (for example, an acetoxy group, a dodecanoyloxy group, an octadecanoyloxy group, a 3-pentadecylphenoxyacetoxy group, a benzoyloxy group, a β-naphthoyloxy group, a 3-[γ-(2,4-di-tert-amylphenoxy)butyramido]benzyloxy group, etc.), an aryloxy group (for example, a phenoxy group, a p-chlorophenoxy group, a p-nitrophenoxy group, a naphthoxy group, etc.), an alkoxy group, a halogen atom (for example, a chlorine atom, a fluorine atom, etc.), an arylazo group (for example, a phenylazo group, a 2-methyl-4-hydroxyphenylazo group, a naphthylazo group, etc.), an aryltriazolyl group (for example, a 1-benzotriazolyl group, a 2-benzotriazolyl group, a 2-naphthotriazolyl group, etc.), an alkylthio group (for example, an alkylthio group having 2 to 22 carbon atoms, etc.), an arylthio group (for example, a phenylthio group, a naphthylthio group, etc.), an aralkoxycarbonyloxy group (for example, a benzyloxycarbonyloxy group, etc.), an alkoxycarbonyloxy group, an aryloxycarbonyloxy group, a heterocyclic thio group (a 2-benzothiazolylthio group, a 1-phenyl-5-tetrazolylthio group, a 2-benzoxazolylthio group, a 2-benzimidazolylthio group, a 5-phenyl-1,3,4-oxadiazolyl-2-thio group, etc.), a cycloalkylthio group (for example, a cyclohexylthio group etc.), a cycloalkoxy group (for example, a cyclohexyloxy group, etc.), an imido group (for example, a phthalimido group, a succinimido group, a 5,5-dimethyl-3-hydantoinyl group, a 5,5-dimethyl-3-oxazolidinyl group, etc.), an imidazolyl group (for example, a 1-imidazolyl group, a 2-methyl-1-imidazolyl group, a 1-benzimidazolyl group, etc.), a pyrazolyl group (for example, 1-pyrazolyl group, a 4-chloro-1-pyrazolyl group, etc.), a triazolyl group (for example, a 3,5-diethyl-1,2,4-1-triazolyl group, etc.), an acylamino group (for example, a benzamido group, an acetylamino group, etc.), a sulfonamido group (for example, a benzenesulfonamido group, a methanesulfonamido group, etc.), a cycloamino group (for example, a piperidino group, a morpholino group, etc.), or the like.

In formula (I), Ar represents an aryl group (for example, a phenyl group or a phenyl group substituted with one or more substituents such as a halogen atom, a cyano group, an alkyl group, an alkoxy group, an acylamino group, a sulfamoyl group, a sulfonamido group, a carbamoyl group, an alkoxycarbonyl group, an alkylsulfonyl group, an alkylthio group, a nitro group, or a trifluoromethyl group, and more preferably a 2-chlorophenyl group, a 4-chlorophenyl group, a 2,5-dichlorophenyl group, a 2,6-dichlorophenyl group, a 2,4,6-trichlorophenyl group, a 2-bromophenyl group, a 3,5-dibromophenyl group, a 2-cyanophenyl group, a 2,6-dichloro-4-cyanophenyl group, a 4-cyanophenyl group, a 4-methylphenyl group, a 2,6-dimethylphenyl group, a 4-butylphenyl group, a 2-trifluoromethylphenyl group, a 2-ethoxyphenyl group, an N-methylbenzamidophenyl group, an N,N-diphenylsulfamoylphenyl group, a phenyl-N-methylsulfonamidophenyl group, a 2,6-dichloro-4-[α-(2,4-di-tert-amylphenoxy)butanamido]phenyl group, a 2,6-dichloro-4-tetradecyloxycarbonylphenyl group, a 2,6-dichloro-4-octadecyloxyphenyl group, a 2,6-dichloro-4-hexadecylthiophenyl group, a 2,6-dichloro-4-octadecylsulfonylphenyl group, a 2,3,4,5,6-pentafluorophenyl group, a 2,3,4,5,6-pentachlorophenyl group, a 2-chloro-5-cyanophenyl group, a 5-chloro-2-methylphenyl group, a 2,6-dichloro-4-methylphenyl group, a 2,4-dichloro-6-methylphenyl group, a 2-chloro-4,6-dimethylphenyl group, a 2,6-dichloro-4-methoxyphenyl group, etc.

The magenta-color-forming couplers represented by formula (I) are novel couplers.

Of these magenta-color-forming couplers employed in the present invention, particularly preferred couplers are those represented by the formula (II)

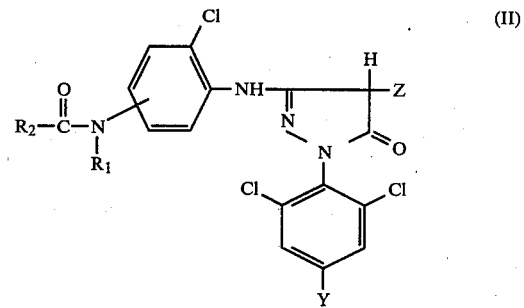

wherein Z, $R_1$, and $R_2$ have the same meanings as defined for formula (I), and the

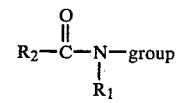

(an N-substituted acylamino group) is preferably present at the 4- or 5-position of the anilino group. Furthermore, for $R_1$ and $R_2$, an alkyl group, an alkenyl group and an aralkyl group as defined for formula (I) are preferred. An unsubstituted alkyl group, an unsubstituted alkenyl group or an unsubstituted aralkyl group is particularly preferred for $R_1$ and $R_2$. Y represents a substituent which is described for the substituent present at the 4-position of the phenyl group described above for Ar in formula (I). Particularly preferred Y groups include hydrogen, a chlorine atom, a cyano group, an acylamino group, a sulfonamino group, an alkoxycarbonyl group, an alkoxycarbonylamino group, an alkylsulfonyl group, or an alkylthio group.

Couplers represented by formula (II) are particularly preferred because the spectral absorption curve of the magenta color images obtained upon color development is sharp, the second absorption zone which is characteristic of conventional pyrazolone type magenta couplers is small, and the melting point thereof is low. Furthermore, the solubility in an organic solvent having a high boiling point is high. Still further, the couplers represented by formula (II) are particularly advantageous since color images are formed therefrom fast, and the formation of yellow stain in the unexposed areas of a color photographic element is less after color development processing upon light irradiation, and the yellow stain does not increase upon light irradiation nor with heat, as is shown in the Examples hereinafter.

5-Pyrazolone type magenta couplers having an N-alkyl-substituted acylamino group in a ballast group are novel couplers. Known ballast groups which have some similar structural features thereto are N-substituted acylamino groups as described in U.S. Pat. No. 3,935,015, succinimido groups as described in U.S. Pat. No. 3,684,514, and alkylamino groups as described in Japanese Patent Application (OPI) No. 123033/74. However, these compounds are structurally different from the couplers according to the present invention, in which the anilino group is substituted with an N-substituted acylamino group. Also, these compounds are inferior to in their photographic properties in comparison with the couplers according to the present invention, as is described in greater detail below.

The magenta-color-forming couplers according to the present invention are advantageous with respect to color reproduction in comparison with the couplers described in U.S. Pat. No. 3,935,015 in which an N-unsubstituted acylamino group is present in a ballast group, since the peak width at half height of the spectral absorption curve of the magenta dye obtained in the present invention is narrow and the hue is close to pure magenta color. Further, the couplers according to the present invention are much superior to the known couplers described above in view of the good light fastness of the color images formed and the minimal amount of the formation of yellow stain at the unexposed areas after color development processing upon irradiation with light. Thus, the couplers according to the present invention are favorable for the preparation of color lightsensitive elements, and in particular for color print light-sensitive elements.

The couplers described in Japanese Patent Application (OPI) No. 123033/74, in which any alkylamino group is present in a ballast group provide magenta dyes in which the maximum absorption peak of the spectral absorption curve is shifted to a shorter wavelength range, and the hue is reddish. On the contrary, the spectral absorption curve of the dyes formed from the couplers according to the present invention are suitable for color reproduction. Furthermore, the couplers according to the present invention are much superior to the known couplers described above in view of the good light fastness of the color images formed, and the small amount of formation of yellow stain at the unexposed areas after color development processing upon light irradiation, and the good stability of the color images and the small amount of the formation of stain during storage for long periods of time under the conditions with temperature and heat.

Specific examples of magenta-color-forming couplers which can be employed in the present invention are shown below, but the present invention is not to be construed as being limited thereto.

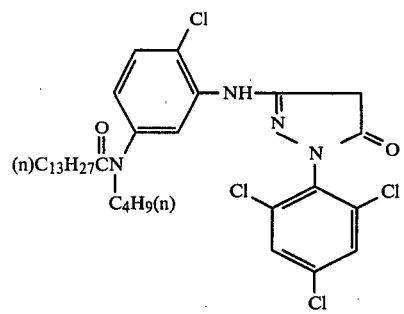
(1)

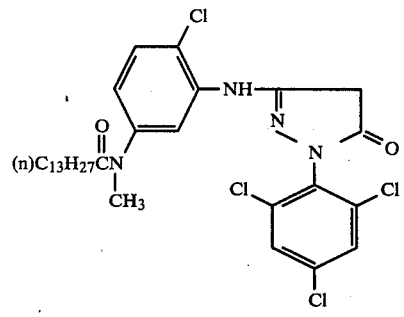
(2)

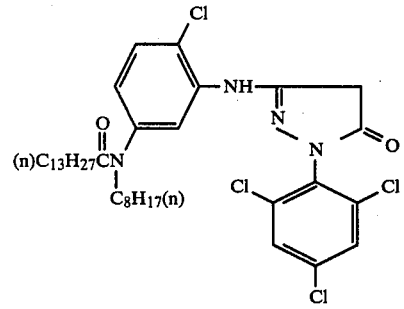
(3)

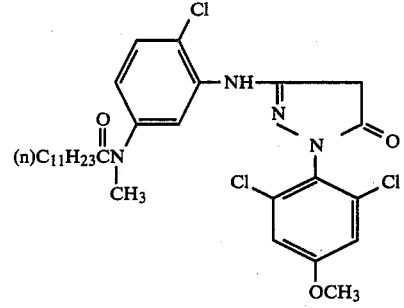
(4)

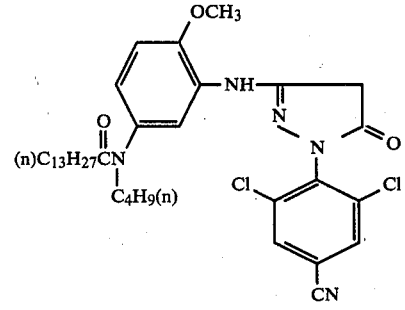
(5)

-continued
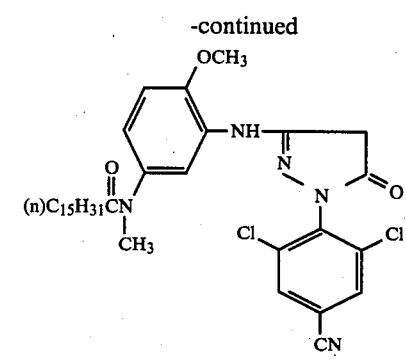
(6)
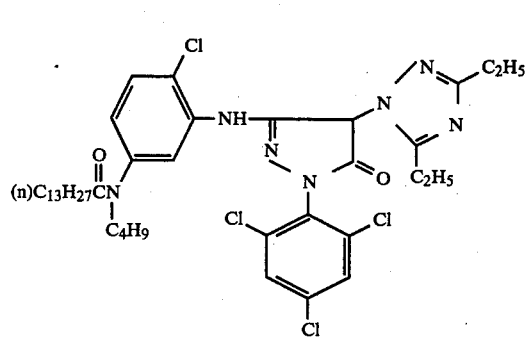
(7)
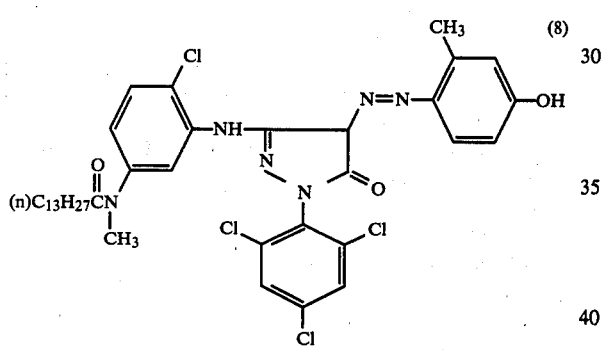
(8)
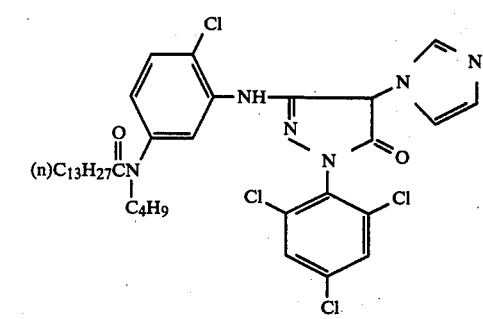
(9)
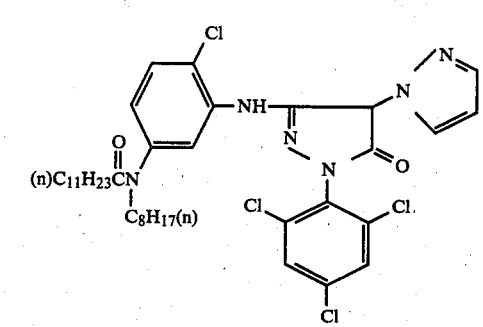
(10)
-continued
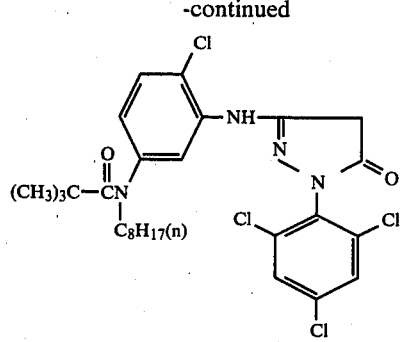
(11)
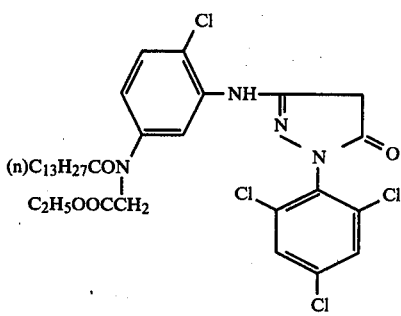
(12)
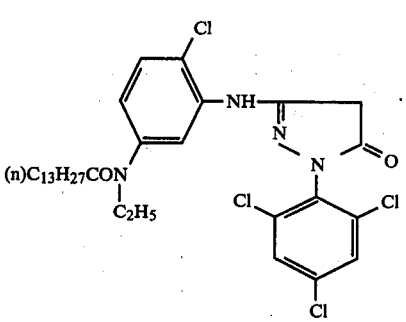
(13)
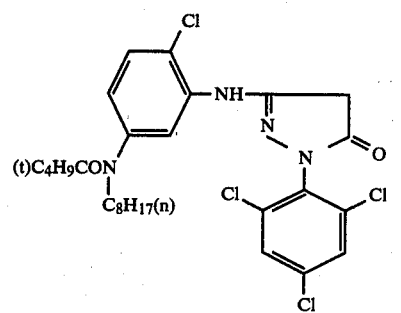
(14)
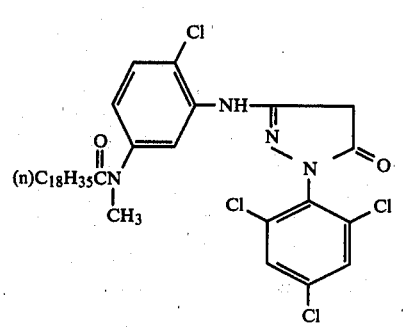
(15)

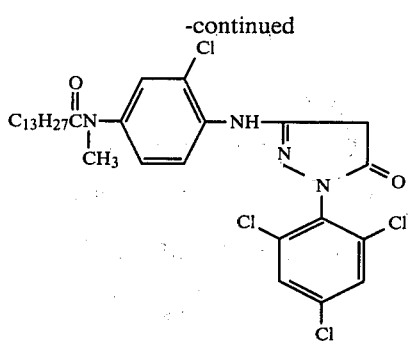

(16)

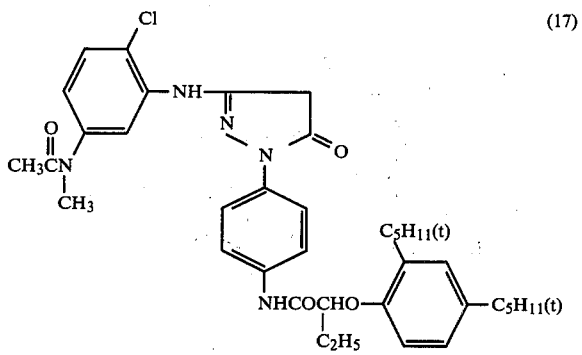

(17)

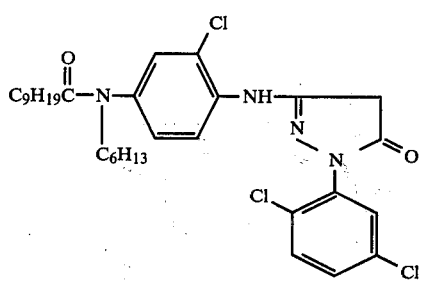

(18)

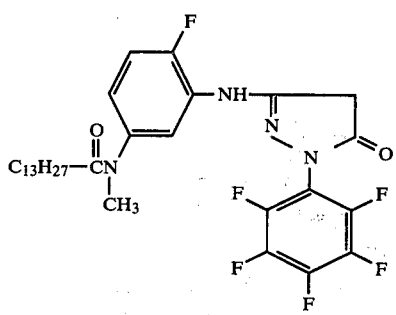

(19)

The N-alkyl-substituted acylamino group of the magenta-color-forming coupler which can be employed in the present invention can be generally synthesized by the following techniques:

(1) Alkylation of an acylamino group using, for example, a method in which an alkyl halide and a strong base, such as sodium hydride, are employed, as described in J.A.C.S. (Journal of the American Chemical Society), Vol. 83, p. 1492 (1961), or the other method in which a quaternary ammonium salt, an alkali, and an alkyl halide are employed, etc., to synthesize an N-alkylsubstituted acylamino group.

(2) Alkylation of an aniline using, for example, a method in which an alkyl halide and potassium hydroxide are used, as described in J.A.C.S., Vol. 82, p. 6163 (1960), a method in which an alkyl halide and pyridine are used as described in Japanese Patent Application (OPI) No. 123033/74, or a method by heating with a Raney nickel catalyst in an alcohol, as described in J.A.C.S., Vol. 76, p. 6174 (1954) to obtain an N-alkyl-substituted aniline, and then the reaction of the thus prepared compound with an acid chloride to synthesize an N-alkyl-substituted acylamino group.

Using the compound having an N-alkyl-substituted acylamino group obtained by the above-described method, the coupler according to the present invention can be synthesized in a similar manner to the production of magenta-color-forming coupler having an N-unsubstituted acylamino group.

Specific synthesis examples for representative magenta-color-forming couplers which can be employed in the present invention are illustrated below. Other compounds can also be synthesized in a similar manner.

SYNTHESIS EXAMPLE 1

Synthesis of
1-(2,4,6-Trichlorophenyl)-3-[2-chloro-5-(N-butyl-tetradecanamino)anilino]-2-pyrazolin-5-one [Coupler (1)]

Step (1)

Synthesis of
2-Chloro-5-(N-butyl-tetradecanoylamino)aniline 36.9 g of 2-chloro-5-(tetradecanoylamino)nitrobenzene, 30 g of butyl iodide and 3.2 g of tetrabutylammonium bromide were dissolved in 100 ml of benzene, and to this solution, a solution containing 30 g of sodium hydroxide dissolved in 50 ml of water was added. The mixture was stirred for 5 hours with heating on a steam bath. After cooling, the organic layer was separated and washed twice with water. The solvent was distilled off under reduced pressure to obtain 42.5 g of an oily product.

The oily product was stirred under refluxing for 2 hours together with 22.4 g of reduced iron powder, 150 ml of isopropanol, 50 ml of water and 2 g of ammonium chloride. After removing the iron powder, the product was concentrated under reduced pressure to obtain 40 g of the desired compound.

Step (2)

Synthesis of
1-(2,4,6-Trichlorophenyl)-3-[2-chloro-5-(N-butyl-tetradecanamino)anilino]-2-pyrazolin-5-one 34 g of the 2-chloro-5-(N-butyl-tetradecanoylamino)aniline, 25.6 g of 1-(2',4',6'-trichlorophenyl)-3-ethoxy-2-pyrazolin-5-one and 2 g of methanesulfonic acid were heated at 150° C. under reduced pressure for 8 hours. After cooling, the mixture was dissolved in ethyl acetate and washed twice with water. The solvent was distilled off and the residue was speared by a silica gel chromatography (using a solvent mixture of ethyl acetate and benzene as a spreading agent) to obtain the desired compound. Upon recrystallization of the compound from a solvent mixture of ethyl acetate and hexane, 23 g of the crystals, having a melting point of 106° to 107° C., were obtained.

Elemental Analysis: Calcd. (%): C: 59.11, H: 6.61, N: 8.36; Found (%): C: 59.27, H: 6.69, N: 8.33.

SYNTHESIS EXAMPLE 2

Synthesis of
1-(2,4,6-Trichlorophenyl)-3-[2-chloro-5-(N-methyl-tetradecanamino)anilino]-2-pyrazolin-5-one [Coupler (2)]

Step (1)

Synthesis of
2-Chloro-5-(N-methyl-tetradecanoylamino)aniline 115 g of 2-chloro-5-(tetradecanoylamino)nitrobenzene, 80 g of methyl iodide and 3 g of tetrabutylammonium bromide were dissolved in 500 ml of toluene and to the solution, a solution containing 45 g of sodium hydroxide dissolved in 60 ml of water was added. The mixture was stirred at 50° C. for 3 hours. After cooling, the organic layer was separated and washed twice with water. The solvent was distilled off under reduced pressure and the residue was crystallized. Upon recrystallization from methanol, 117 g of the crystals were obtained.

The above-described crystals, 62 g of reduced iron powder, 5 g of ammonium chloride, 500 ml of isopropanol and 100 ml of water were mixed and stirred for 1 hour under refluxing. After removing the iron powder, to the reaction mixture ethyl acetate was added and was washed three times with water. By removing the solvent 104.5 g of the oily product was obtained. Upon crystallization of the oily product from cool hexane, the crystals having a melting point of 49° to 50° C. were obtained.

Step (2)

Synthesis of
1-(2,4,6-Trichlorophenyl)-3-[2-chloro-5-(N-methyl-tetradecanamino)anilino]-2-pyrazolin-5-one 36 g of the 2-chloro-5-(N-methyl-tetradecanoylamino)aniline, 31 g of 1-(2,4,6-trichlorophenyl)-3-ethoxy-2-pyrazolin-5-one and 3 g of methanesulfonic acid were heated at 150° C. under reduced pressure for 9 hours. After cooling, acetonitrile was added to the reaction mixture and allowed to stand. The crystals were removed by filtration and the filtrate was concentrated and separated by silica gel chromatography (using a solvent mixture of ethyl acetate and benzene as a spreading agent) to obtain the desired compound. Upon recrystallization from acetonitrile, 40 g of the crystals, having a melting point of 124° to 126° C., were obtained.

Elemental Analysis: Calcd. (%): C: 57.33 H: 6.10 N: 8.92; Found (%): C: 57.12 H: 6.13 N: 8.79.

The magenta-color-forming coupler in accordance with the present invention possesses both high coupling activity and sufficient solubility in an organic solvent, and, therefore, a color photographic element prepared using this coupler provides desirable photographic properties, such as a good sensitivity, gradation and the like, and possesses the characteristic that the photograhic element is easy to prepare. Moreover, the color photographic element has the characteristics that not only does the photographic color image obtained by the development processing thereof possess a spectral absorption characteristic which is effective for color reproduction and sufficient light fastness, but also, after color development processing, yellow stain is reduced in the unexposed portions, and increase in the yellow stain is minimal even on exposure to light for a long period of time. Furthermore, fading of the photographic color images due to light is greatly reduced.

Furthermore, the magenta color image obtained from the coupler in accordance with the present invention is resistant to the adverse actions of heat and humidity. That is, the degree of color fading due to heat is serious with color images formed from 5-pyrazolones having an acylamino group or a ureido group at the 3-position thereof. This is believed to be due to the fact that the dyes formed react with the remaining coupler to produce a colorless product. For preventing color fading, a processing using a stabilizing solution containing formaldehyde or the like has been practiced, in general. A characteristic of the coupler of the present invention is that sufficient fastness is obtained without such processing being necessary.

In order to prepare a silver halide color photographic light-sensitive element using the coupler of the present invention, a coupler according to the present invention can be used individually, two or more couplers according to the present invention can be used as a mixture thereof, or a coupler according to the present invention can be used in combination with known magenta color image-forming couplers. Further, in order to enhance the color reproduction of color photographic light-sensitive elements, magenta couplers according to the present invention can also be used in the same emulsion layer in combination with a cyan- or yellow-color-forming coupler which has a different hue, e.g., as described in Japanese Patent Publication No. 391/65.

PYrazolone type compounds, indazolone type compounds, cyanoacetyl compounds, etc., can be employed as magenta-color-forming couplers in addition to the couplers according to the present invention, and particularly preferred couplers are pyrazolone type compounds. Specific examples of such magenta-color-forming couplers which can be employed are those described, for example, in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, German Pat. No. 1,810,464, German Patent Application (OLS) Nos. 2,408,665, 2,417,945, 2,418,959 and 2,424,467, Japanese Patent Publication No. 6031/65, Japanese Patent Application (OPI) Nos. 20826/76, 58922/77, 129538/74, 74027/74, 159336/75, 42121/77, 74028/74, 60233/75, 26541/76, and 55122/78, and so forth.

Known open chain ketomethylene type couplers can be used as yellow-color-forming couplers in color photographic light-sensitive elements according to the present invention. Of these couplers, benzoyl acetanilide type and pivaloyl acetanilide type compounds are especially effective. Specific examples of yellow-color-forming couplers which can be employed are described, for example, in U.S. Pat. Nos. 2,875,057, 3,265,506, 3,408,194, 3,551,155, 3,582,322, 3,725,072 and 3,891,445, German Pat. No. 1,547,868, German Patent Application (OLS) Nos. 2,219,917, 2,261,361 and 2,414,006, British Pat. No. 1,425,020, Japanese Patent Publication No. 10783/76, Japanese Patent Application (OPI) Nos. 26133/72, 73147/73, 102636/76, 6341/75, 123342/75, 130442/75, 21827/76, 87650/75, 82424/77 and 115219/77, and so forth.

Phenol type compounds, naphthol type compounds, etc., can be employed as cyan-folor-forming couplers. Specific examples of cyan-color-forming couplers which can be employed are those described, for example, in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, German Patent Application (OLS) Nos. 2,414,830 and 2,454,329, Japanese Patent Application (OPI) Nos. 59838/73, 26034/76, 5055/73, 146828/76, 69624/77 and 90932/77, and so forth.

Colored couplers which can be employed are described, for example, in U.S. Pat. Nos. 3,476,560, 2,521,908 and 3,034,892, Japanese Patent Publication Nos. 2016/69, 22335/63, 11304/67 and 32461/69, Japanese Patent Application (OPI) Nos. 26034/76 and 42121/77, and German Patent Application (OLS) No. 2,418,959.

Development inhibitor releasing (DIR) couplers which can be employed are described, for example, in U.S. Pat. Nos. 3,227,554, 3,617,291, 3,701,783, 3,790,384 and 3,632,345, German Patent Application (OLS) Nos. 2,414,006, 2,454,301 and 2,454,329, British Pat. No. 953,454, Japanese Patent Application (OPI) Nos. 69624/77, 122335/74, and Japanese Patent Publication No. 16141/76.

In addition to IDR couplers, other compounds which release development inhibitors upon development can also be present in the light-sensitive material. For example, DIR compounds as described, for example, in U.S. Pat. Nos. 3,297,445 and 3,379,529, German Patent Application (OLS) No. 2,417,914, Japanese Patent Application (OPI) Nos. 15271/77 and 9116/78, etc., can be employed.

Two or more kinds of the couplers described above can be incorporated in the same layer or the same coupler compound can also be present in two or more layers.

These couplers are incorporated into the emulsion layers, generally in an amount of from about $2 \times 10^{-3}$ mol to about $5 \times 10^{-1}$ mol, preferably $1 \times 10^{-2}$ mol to $5 \times 10^{-1}$ mol, per mol of silver.

Conventional methods, e.g., the method described in U.S. Pat. No. 2,322,027, can be employed to incorporate the couplers into the silver halide emulsion layers. For example, the couplers can be dissolved in phthalic acid alkyl esters (e.g., dibutyl phthalate, dioctyl phthalate, etc.), phosphoric acid esters (e.g., diphenyl phosphate, triphenyl phosphate, tricresyl phosphate, dioctylbutyl phosphate), citric acid esters (e.g., tributyl acetylcitrate), benzoic acid esters (e.g., octyl benzoate), alkyl amides (e.g., diethyl laurylamide), fatty acid esters (e.g., dibutoxyethyl succinate, dioctyl azelate), etc.; or an organic solvent having a relatively low boiling point of from about 30° to 150° C. such as a lower alkyl acetate (e.g., ethyl acetate, butyl acetate, etc.), ethyl propionate, sec-butyl alcohol, methyl isobutyl ketone, β-ethoxyethyl acetate, methyl Cellosolve acetate. Then the solution is dispersed in a hydrophilic colloid. The above-described organic solvents having a high boiling point and the above-described organic solvents having a low boiling point may be used as mixtures, if desired.

Furthermore, the dispersing method using a polymeric material as described in Japanese Patent Publication No. 39853/76, Japanese Patent Application (OPI) No. 59943/76 can also be used.

When couplers having an acid group, such as a carboxylic acid group, a sulfonic acid group, etc., are used, they can be incorporated in a hydrophilic colloid as an alkaline aqueous solution thereof.

The photographic emulsion used in this invention can be prepared using the methods described in, e.g., P. Glafkides, *Chemie et Physique Photographique*, Paul Montel, Paris (1967), G. F. Duffin, *Photographic Emulsion Chemistry*, The Focal Press, London (1966), V. L. Zelikman, et al., *Making and Coating Photographic Emulsions*, The Focal Press, London (1964), etc. That is, any of the acid method, the neutral method, the ammonia method and other methods can be used. Moreover, a soluble silver salt can be reacted with a soluble halogen salt using any of the single jet method, the double jet method and a combination thereof.

A method in which grains are formed in the presence of an excess of silver ions (i.e., the so-called reverse mixing method) can also be used. As one of the modes of the double jet method, the method in which the pAg of the liquid phase in which the silver halide is to be produced is kept constant, that is, the so-called controlled double jet method, can be used. This method can provide silver halide emulsions having a regular crystal form and an almost uniform grain size.

Two or more silver halide emulsions which are separately prepared can be mixed and then used, if desired.

In the process of the formation of the silver halide grains or physical ripening, cadmium salts, zinc salts, lead salts, thallium salts, iridium salts or complex salts thereof, rhodium salts or complex salts thereof, iron salts or iron complex salts, and the like can be present.

Gelatin can advantageously be used as the binder or protective colloid for the photographic emulsion used in this invention. However, other hydrophilic colloids can be used as well. For example, proteins such as gelatin derivatives, graft polymers between gelatin and other high polymers, albumin, casein, etc.; cellulose derivatives such as hydroxyethyl cellulose, carboxymethyl cellulose, cellulose sulfates, etc.; saccharide derivatives such as sodium alginate, starch derivatives, etc.; and various synthetic hydrophilic high polymers of homo- or copolymers such as polyvinyl alcohol, polyvinyl alcohol partial acetal, poly-N-vinylpyrrolidone, polyacrylic acid, polymethacrylic acid, polyacrylamide, polyvinylimidazole, polyvinylpyrazole, etc., can be used as the binder or protective colloid for the photographic emulsion.

Acid-processed gelatin and enzyme-processed gelatin as described in *Bull. Soc. Sci. Photo. Japan*, No. 16, p. 30 (1966) can be used as well as lime-processed gelatin as the gelatin component. In addition, the hydrolyzed products of gelatin and enzyme-decomposed products of gelatin are also suitable. Suitable gelatin derivatives which can be used include those obtained by reacting gelatin with various compounds, such as acid halides, acid anhydrides, isocyanates, bromoacetic acid, alkanesultones, vinylsulfonamides, maleinimides, polyalkylene oxides, epoxy compounds, etc. Specific examples thereof are described in U.S. Pat. Nos. 2,614,928, 3,132,945, 3,186,846, 3,312,553, British Pat. Nos. 861,414, 1,033,189, 1,005,784, Japanese Patent Publication No. 26845/67.

As the above-described gelatin graft polymer, those which are obtained by grafting homo- or copolymers of vinyl monomers such as acrylic acid, methacrylic acid, the ester or amide derivatives thereof, acrylonitrile, styrene, etc., to gelatin can be used. In particular, graft polymers with a polymer having some compatibility with gelatin, such as polymers of acrylic acid, methacrylic acid, acrylamide, methacrylamide, hydroxyalkyl methacrylates, etc., are preferred. Examples thereof are described in U.S. Pat. Nos. 2,763,625, 2,831,767, 2,956,884, etc. Typical synthetic hydrophilic materials are described in, e.g., German Patent Application (OLS) No. 2,312,708, U.S. Pat. Nos. 3,620,751, 3,879,205 and Japanese Patent Publication No. 7561/68.

For the purposes of preventing fog or stabilizing the photographic properties during preparation, storage, and/or photographic processing of light-sensitive materials, a variety of compounds can be incorporated into photographic emulsions used according to the present invention. For example, a wide variety of compounds which are known as anti-fogging agents or stabilizers, such as azoles, e.g., benzothiazolium salts, nitrobenzimidazoles, nitroindazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (especially 1-phenyl-5-mercaptotetrazole), etc.; mercaptopyrimidines; mercaptotriazines; thioketo compounds, such as oxazolinethione; azaindenes, e.g., triazaindenes, tetrazaindenes (especially 4-hydroxy-substituted (1,3,3a,7)-tetrazaindenes), pentazaindenes, etc.; benzenethiosulfonic acid, benzenesulfinic acid, benzenesulfonic amide, etc., can be used. For example, the compounds as described in U.S. Pat. Nos. 3,954,474 and 3,982,947, Japanese Patent Publication No. 28660/77 can be used.

For the purpose of increasing sensitivity, increasing contrast, or accelerating development, photographic emulsion layer of the photographic light-sensitive element according to the present invention can contain other known additives, such as, for example, polyalkylene oxides or derivatives thereof such as ethers, esters, amines, etc., thioether compounds, thiomorpholine compounds, quaternary ammonium compounds, urethane derivatives, urea derivatives, imidazole derivatives, 3-pyrazolidones, etc. For example, such additives as described in U.S. Pat. Nos. 2,400,532, 2,423,549, 2,716,062, 3,617,280, 3,772,021, 3,808,003, British Pat. No. 1,488,991, etc.

The photographic emulsion layers and other hydrophilic colloid layers of the light-sensitive material prepared in accordance with the present invention can contain whitening agents, such as stilbenes, triazines, oxazoles, or coumarins, etc. These agents can be water-soluble or can also be employed as a dispersion of water-insoluble whitening agents. Specific examples of fluorescent whitening agents are described in U.S. Pat. Nos. 2,632,701, 3,269,840 and 3,359,102, and Brish Pat. Nos. 852,075 and 1,319,765.

The hydrophilic colloid layers of the light-sensitive material prepared according to the present invention can contain water-soluble dyes such as filter dyes or for various purposes of preventing irradiation or other purposes. Such dyes include oxonol dyes, hemioxonol dyes, styryl dyes, merocyanine dyes, cyanine dyes and azo dyes. Of these dyes, oxonol dyes, hemioxonol dyes and merocyanine dyes are especially useful. Specific examples of such dyes which can be employed are described, for example, in British Pat. Nos. 584,609 and 1,177,429, Japanese Patent Application (OPI) Nos. 85130/73, 99620/74, 114420/74 and 108115/77, and U.S. Pat. Nos. 2,274,782, 2,533,472, 2,956,879, 3,148,187, 3,177,078, 3,247,127, 3,540,887, 3,575,704, 3,653,905, 3,718,472, 4,071,312 and 4,070,352.

The photographic emulsion of the present invention can also be spectrally sensitized with methane dyes of other dyes. Suitable dyes which can be employed include cyanine dyes, merocyanaine dyes, complex cyanine dyes, complex merocyanine dyes, holopolar cyanine dyes, hemicyanine dyes, styryl dyes, and hemioxonol dyes. Of these days, cyanine dyes, merocyanine dyes and complex merocyanine dyes are particularly useful. Any conventionally utilized nucleus for cyanine dyes, such as basic heterocyclic nuclei, is applicable to these dyes. That is, a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus, etc., and further, nuclei formed by fusing alicyclic hydrocarbon rings with these nuclei and nuclei formed by condensing aromatic hydrocarbon rings with these nuclei, that is, an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus, a quinoline nucleus, etc., are appropriate. The carbon atoms of these nuclei can also be substituted.

Among merocyanine dyes that can be employed are complex merocyanine dyes containing 5- or 6-membered heterocyclic nuclei such as a pyrazolin-5-one nucleus, a thiohydantoin nucleus, a 2-thioxazolidin-2,4-dione nucleus, a thiazolidin-2,4-dione nucleus, a rhodanine nucleus, a thiobarbituric acid nucleus, and so forth.

Useful sensitizing dyes include those described in German Pat. No. 929,080, U.S. Pat. Nos. 2,231,658, 2,493,748, 2,503,776, 2,519,001, 2,912,329, 3,656,959, 3,672,897, 3,694,217, 4,025,349 and 4,046,572, British Patent 1,242,588, Japanese Patent Publication Nos. 14030/69 and 24844/77, and so forth.

These sensitizing dyes can be employed individually, and can also be employed in combination. A combination of sensitizing dyes is often used particularly for the purpose of supersensitization.

Representative examples thereof are described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707, British Pat. Nos. 1,344,281, and 1,507,803, Japanese Patent Publication Nos. 4936/68, and 12375/78, and Japanese Patent Application (OPI) Nos. 110618/77 and 109925/77.

The sensitizing dyes may be present in the emulsion together with dyes which themselves do not give rise to spectrally sensitizing effects but exhibit a supersensitizing effect or materials which do not substantially absorb visible light but exhibit a supersensitizing effect. For example, aminostilbene compounds substituted with a nitrogen-containing heterocyclic ring group (e.g., those described in U.S. Pat. Nos. 2,933,390 and 3,635,721), aromatic organic acid-formaldehyde condensates (e.g., those described in U.S. Pat. No. 3,743,510), cadmium salts, azaindene compounds, and the like, can be present. The combinations described in U.S. Pat. Nos. 3,615,613, 3,615,641, 3,617,295 and 3,635,721 are particularly useful.

The present invention is also applicable to multilayer multicolor photographic materials containing layers sensitive to at least two different spectral wavelength ranges on a support. A multilayer color photographic material generally possesses at least one red-sensitive silver halide emulsion layer, at least one green-sensitive silver halide emulsion layer and at least one blue-sensitive silver halide emulsion layer, respectively, on a support. The order of these layers can be varied optionally as desired. Ordinarily, a cyan-forming coupler is present in a red-sensitive emulsion layer, a magenta-forming coupler is present in a green-sensitive emulsion layer and a yellow-forming coupler is present in a blue-sensitive emulsion layer, respectively. However, if desired, a different combination can be employed.

Light-sensitive elements prepared according to the present invention can also contain, as color fog preventing agents, hydroquinone derivatives, aminophenol derivatives, gallic acid derivatives, ascorbic acid derivatives, or the like. Specific examples of these agents are described in U.S. Pat. Nos. 2,360,290, 2,336,327, 2,403,721, 2,418,613, 2,675,314, 2,701,197, 2,704,713, 2,728,659, 2,732,300 and 2,735,765, Japanese Patent Application (OPI) Nos. 92988/75, 92989/75, 93928/75, 110337/75 and 146235/77, Japanese Patent Publication No. 23813/75, and so forth.

The hydrophilic colloid layers of the light-sensitive elements prepared in accordance with the present invention can also contain UV absorbents. For example, benzotriazole compounds substituted with aryl groups (e.g., those described in U.S. Pat. No. 3,533,794), 4-thiazolidone compounds (e.g., those described in U.S. Pat. Nos. 3,314,794 and 3,352,681), benzophenone compounds (e.g., those described in Japanese Patent Application (OPI) No. 2784/71), cinnamic acid ester compounds (e.g., those described in U.S. Pat. Nos. 3,707,375 and 3,705,805), butadiene compounds (e.g., those described in U.S. Pat. No. 4,045,229) or benzoxazole compounds (e.g., those described in U.S. Pat. No. 3,700,455) can be employed. Furthermore, the compounds as described in U.S. Pat. No. 3,499,762, Japanese Patent Application (OPI) No. 48535/79 can also be used. UV absorbing couplers (e.g., α-naphthol type cyan-color-forming couplers) and UV absorbing polymers can also be employed. These UV absorbents can also be mordanted in a specific layer(s), if desired.

In the practice of the present invention, known color fading preventing agents as described below can be employed. These fading preventing agents can be used individually or in a combination of two or more thereof. Specific examples of known color fading preventing agents include, for example, hydroquinone derivatives as described in U.S. Pat. Nos. 2,360,290, 2,418,613, 2,675,314, 2,701,197, 2,704,713, 2,728,659, 2,732,300, 2,735,765, 2,710,801 and 2,816,028, British Pat. No. 1,363,921; gallic acid derivatives as described in U.S. Pat. Nos. 3,457,079 and 3,069,262; p-alkoxyphenols as described in U.S. Pat. Nos. 2,735,765 and 3,698,909, Japanese Patent Publication Nos. 20977/74 and 6623/77; p-oxyphenol derivatives as described in U.S. Pat. Nos. 3,432,300, 3,573,050, 3,574,627 and 3,764,337, Japanese Patent Application (OPI) Nos. 35633/77, 147434/77 and 15222/77; bisphenol derivatives as described in U.S. Pat. No. 3,700,455, etc.

Known methods can be used for processing the light-sensitive material according to the present invention. Known processing solutions can be used. The processing temperature can be between about 18° C. and about 50° C., in general, but temperatures lower than about 18° C. or higher than about 50° C. may be used, if desired. Either a development processing for forming silver images (black-and-white photographic processing) or a color photographic processing comprising developing processing for forming dye images can be employed, as desired.

Among methods that can be employed are a negative-positive method (for example, as described in *Journal of the Society of Motion Picture and Television Engineers*, Vol. 61, pp. 667–701 (1953); a color reversal method which comprises developing with a developer containing a black-and-white developing agent to form a negative silver image, then subjecting the photographic material to at least one uniform exposure or to another appropriate fogging treatment, and subsequently performing color development to obtain positive dye images; and a silver dye bleaching method which comprises exposing a dye-containing photographic emulsion layer and developing the same to form a silver image and then bleaching the dyes using the silver image as a bleaching catalyst.

The color developer generally comprises an alkaline aqueous solution containing a color developing agent. Suitable color developing agents which can be employed include known primary aromatic amine developing agents, e.g., phenylenediamines (e.g., 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfamidoethylaniline, 4-amino-3-methyl-N-ethyl-N-β-methoxyethylaniline, etc.).

In addition, developing agents described in L.F.A. Mason, *Photographic Processing Chemistry*, at pages 226 to 229, Focal Press (1966), U.S. Pat. Nos. 2,193,015 and 2,592,364, Japanese Patent Application (OPI) No. 64933/73, etc., can be employed.

The color developers can also contain pH buffering agents, such as sulfites, carbonates, borates and phosphates of alkali metals, developing inhibitors or anti-fogging agents such as bromides, iodides or organic anti-fogging agents, etc. In addition, if desired, the color developers can also contain water softeners, preservatives such as hydroxylamine; organic solvents such as benzyl alcohol, diethylene glycol, etc.; developing accelerators such as polyethylene glycol, quaternary ammonium salts, amines; dye-forming couplers; competing couplers; fogging agents such as sodium borohydride; auxiliary developers such as 1-phenyl-3-pyrazolidone; viscosity-imparting agents; polycarboxylic acid type chelating agents described in U.S. Pat. No. 4,083,723; anti-oxidizing agents as described in German Patent Application (OLS) No. 2,622,950; and the like.

The photographic emulsion layers after color development are generally bleach-processed. Bleach processing can be performed at the same time as fixing, or separately therefrom. Suitable bleaching agents which can be employed are compounds of polyvalent metals such as iron (III), cobalt (IV), chromium (VI), copper (II), etc., peracids, quinones, nitroso compounds, etc. Specific examples include ferricyanides; bichromates; organic complexes of iron (III) or cobalt (III); aminopolycarboxylic acids such as ethylenediaminetetraacetic acid, nitriloriacetic acid, 1,3-diamino-2-propanol tetraacetic acid, etc.; complexes of organic acids such as citric acid, tartaric acid, malic acid, etc.; persulfates; permanganates; nitrosophenol; etc. Of these, particularly useful bleaching agents are potassium ferricyanide, sodium ethylenediaminetetraacetate iron (III) and ammonium ethylenediaminetetraacetate iron (III). Ethylenediamine tetraacetate iron (III) complex is useful both in a bleaching solution and in a mono bath bleach-fixing solution.

Bleaching and bleach-fixing solutions can contain various additives, including bleach accelerating agents as described in U.S. Pat. Nos. 3,042,520 and 3,241,966, Japanese Patent Publication Nos. 8506/70 and 8836/70, thioether compounds as described in Japanese Patent Application (OPI) No. 65732/78, and the like.

The light-sensitive material prepared using the present invention may be subjected to processing with a developing solution which is replenished or otherwise maintains its properties by the methods as described in Japanese Patent Application (OPI) Nos. 84636/76, 119934/77, 46732/78, 9626/79, 19741/79 and 37731/79, Japanese Patent Application Nos. 76158/79, 76159/79 and 102962/79, etc.

The light-sensitive material prepared using the present invention may be processed with a bleach-fixing solution which can be subjected to regeneration treatment, such as by methods as described in Japanese Patent Application (OPI) Nos. 781/71, 49437/73, 18191/73, 145231/75, 18541/76, 19535/76 and 144620/76, Japanese Patent Publication No. 23178/76, etc.

The characteristics obtained by employing the magenta-color-forming coupler of the present invention are more specifically explained below by reference to some specific examples. For comparison, the magenta couplers indicated below are used.

Comparison Coupler (a)

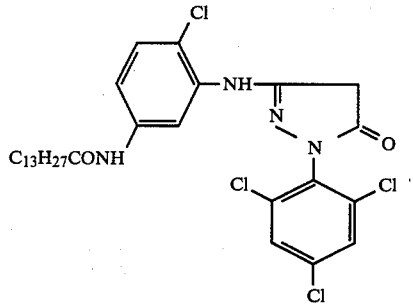

Comparison Coupler (b)

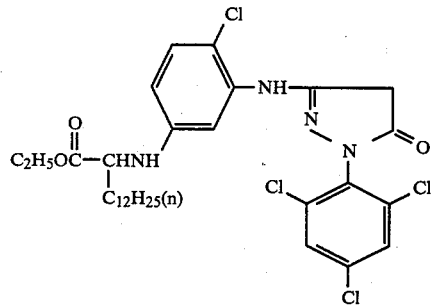

With Comparison Couplers (a) and (b) indicated above and with Couplers (1) and (8) according to the present invention, the spectral absorption characteristics of the azomethine dye formed by the oxidation-coupling reaction with 4-[N-ethyl-N-($\beta$-methanesulfonamidoethyl)]-amino-2-methylaniline were measured in ethyl acetate and compared.

From the spectral absorption curves obtained, the color density of the main wavelength was adjusted to 1.00, and the density of a second absorption appearing in the blue light region, the density at a longer wavelength of 60 nm from the main wavelength and the width of the wavelength at which the color density became 0.50 were determined. The results obtained are shown in Table 1 below.

TABLE 1

| | Peak of Main Wavelength (nm) | Color Density of Second Absorption | Color Density at 60 nm Longer Wavelength | Width (nm) of Wavelength Having Density of 0.5 |
|---|---|---|---|---|
| Coupler (1) Present Invention | 530 | 0.138 | 0.128 | 65 |
| Comparison Coupler(a) | 529 | 0.141 | 0.134 | 67 |
| Comparison Coupler(b) | 526 | 0.142 | 0.133 | 69 |
| Coupler (8) Present Invention | 529 | 0.139 | 0.127 | 65 |

The color image obtained using the coupler of the present invention has a sharp cut-off at the long wavelength side of the peak, and undesired second absorption is minimal. Furthermore, the position of the main wavelength is appropriate for good color reproduction. While the reasons for these desirable properties are not fully understood, they are believed to result because the coupler of the present invention possesses a chlorine atom at the 2-position of and an N-substituted acylamino group at the 5-position of the anilino ring thereof.

The characteristics obtained using the magenta coupler of the present invention are explained further by reference to the examples hereinbelow.

EXAMPLE 1

10 g of Coupler (1) of the present invention was dissolved in 10 ml of tricresyl phosphate and 10 ml of ethyl acetate and the solution was dispersed in 80 g of a 10% aqueous gelatin solution containing sodium dodecylbenzenesulfonate. Thus-prepared dispersion was mixed with 145 g of a green-sensitive silver chlorobromide emulsion (50 mol% silver bromide) containing 7 g of silver, and sodium dodecylbenzenesulfonate was added thereto as a coating aid. The mixture was coated on a paper support both surfaces of which were laminated with polyethylene and dried (Sample A).

Samples (B) to (F) were prepared in a manner similar to the preparation of Sample (A) except that couplers (2), (5) and (14) of the present invention and Comparison Couplers (a) and (b) were employed, respectively.

These samples were exposed to light of 1,000 lux/sec using a sensitometer and processed with the following color developer solution.

| Color Developer Solution | |
|---|---|
| Benzyl Alcohol | 15 ml |
| Diethylene Glycol | 8 ml |
| Ethylenediaminetetraacetic Acid | 5 g |
| Sodium Sulfite | 2 g |
| Anhydrous Potassium Carbonate | 30 g |
| Hydroxylamine Sulfate | 3 g |
| Potassium Bromide | 0.6 g |
| 4-Amino-N-ethyl-N-($\beta$-methanesulfonamidoethyl)-m-toluidine Sesquisulfate Monohydrate | 5 g |
| Adjust pH to 10.20 | |
| Water to make | 1 l |
| Bleach-Fixing Solution | |
| Ethylenediaminetetraacetic Acid | 2 g |
| Ferric Salt of Ethylenediaminetetraacetate | 40 g |
| Sodium Sulfite | 5 g |
| Ammonium Thiosulfate | 70 g |
| Water to make | 1 l |

-continued (pH 6.8)

| Processing Step | Temperature (°C.) | Time |
|---|---|---|
| 1. Color Development | 33 | 3 min 30 sec |
| 2. Bleach-Fixing | 33 | 1 min 30 sec |
| 3. Washing with Water | 25 to 30 | 2 min 30 sec |

Each sample thus-processed with a dye image was subjected to fading testing for 2 weeks using a fluorescent lamp fading tester (20,000 lux) equipped with an ultraviolet light absorbing filter capable of absorbing substantially all ultraviolet lights having a wavelength of 400 nm or less (manufactured by Fuji Photo Film Co., Ltd.). The results obtained are shown in Table 2 below.

TABLE 2

| Sample No. | Coupler Used | Change of Yellow Stain Density in White Background | Change of Magenta Density (Initial Density of 1.0) |
|---|---|---|---|
| A | Coupler (1) Present Invention | +0.07 | −0.32 |
| B | Coupler(2) Present Invention | +0.06 | −0.26 |
| C | Coupler(5) Present Invention | +0.06 | −0.27 |
| D | Coupler(14) Present Invention | +0.06 | −0.26 |
| E | Comparison Coupler(a) | +0.17 | −0.53 |
| F | Comparison Coupler(b) | +0.19 | −0.62 |

EXAMPLE 2

On a paper support both surfaces of which were laminated with polyethylene were coated a first layer (undermost layer) to a sixth layer (uppermost layer) as shown in Table 3 in order to prepare a color light-sensitive material. A coating composition for a third layer was prepared in accordance with the procedure as described in Example 1. Thus samples were prepared using the couplers as shown in Table 4.

TABLE 3

| Sixth Layer: (protective layer) | Gelatin (1,000 mg/m$^2$) |
|---|---|
| Fifth Layer: (red-sensitive layer) | Silver chlorobromide emulsion (Br: 50 mol %), Silver (300 mg/m$^2$), Gelatin (1,000 mg/m$^2$), Cyan coupler*$^1$ (400 mg/m$^2$), Coupler solvent*$^2$ (200 mg/m$^2$) |
| Fourth Layer: (interlayer) | Gelatin (1,200 mg/m$^2$), Ultraviolet light-absorbing agent*$^3$ (1,000 mg/m$^2$), Ultraviolet light-absorbing agent solvent*$^2$ (250 mg/m$^2$) |
| Third Layer: (green-sensitive layer) | Silver chlorobromide emulsion (Br: 50 mol %), Silver (290 mg/m$^2$), Gelatin (1,000 mg/m$^2$), Magenta coupler (200 mg/m$^2$), Coupler solvent*$^4$ (200 mg/m$^2$) |

TABLE 3-continued

| Second Layer: (interlayer) | Gelatin (1,000 mg/m$^2$) |
|---|---|
| First Layer: (blue-sensitive layer) | Silver chlorobromide emulsion (Br: 80 mol %), Silver (400 mg/m$^2$), Gelatin (1,200 mg/m$^2$), Yellow coupler*$^5$ (300 mg/m$^2$), Coupler solvent*$^6$ (150 mg/m$^2$) |
| Support: | Paper support, both surfaces of which were laminated with polyethylene |

*$^1$Coupler: 2-[α-(2,4-Di-tert-pentylphenoxy)butanamido]-4,6-dichloro-5-methylphenol
*$^2$Solvent: Dibutyl phthalate
*$^3$Ultraviolet light-absorbing agent: 2-(2-Hydroxy-3-sec-butyl-5-tert-butylphenyl)-benzotriazole
*$^4$Solvent: Tricresyl phosphate
*$^5$Coupler: α-Pivaloyl-α-(2,4-dioxo-5,5'-dimethyloxy-azolidin-3-yl)-2-chloro-5-[α-(2,4-di-tert-pentylphenoxy)butanamido]acetanilide
*$^6$Solvent: Dioctyl butyl phosphate These samples were exposed using a sensitometer to light of 1,000 lux/sec equipped with a green filter, SP-2 (made by Fuji Photo Film Co., Ltd.). Then, these samples were subjected to the same processing as described in Example 1.

Each sample having a dye image thus-formed was subjected to fading testing for 4 weeks using a fluorescent lamp fading tester (20,000 lux). The results obtained are shown in Table 4 below.

TABLE 4

| Sample No. | Couplers and Color Image Stabilizers Used | Change of Yellow Stain Density in White Background | Change of Magenta Density (Initial Density of 1.0) |
|---|---|---|---|
| L | Coupler (1) Present Invention Color Image Stabilizer (d) Color Image Stabilizer (e) | +0.06 | −0.26 |
| M | Comparison Coupler (a) Color Image Stabilizer (d) Color Image Stabilizer (e) | +0.15 | −0.39 |

While the invention has been described in detail and with reference to specific embodiments thereof, it will be apparent to one skilled in the art that various changes and modifications can be made therein without departing from the spirit and scope thereof.

What is claimed is:

1. A color photographic light-sensitive element comprising a support having thereon a silver halide emulsion layer containing therein a 3-anilino-5-pyrazolone magenta-color-forming coupler represented by formula (I)

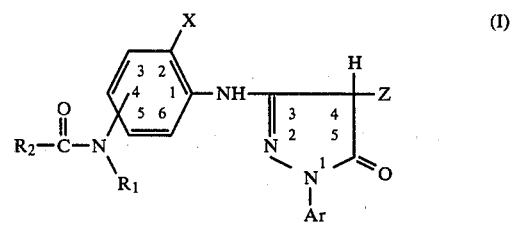

wherein

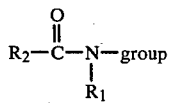

(an N-substituted acylamino group) is present at the 4- or 5-position of the anilino group; $R_1$ represents a substituted or unsubstituted alkyl group, an alkenyl group, a cycloalkyl group, a cycloalkenyl group, or an aralkyl group; $R_2$ represents an aliphatic hydrocarbon group, a heterocyclic group, or an aryl group; X represents a halogen atom or an alkoxy group; Z represents hydrogen or a coupling-off group; and Ar represents an aryl group.

2. A color photographic light-sensitive element as in claim 1, wherein $R_1$ represents a straight chain or branched chain alkyl group having 1 to 22 carbon atoms, an alkenyl group having 2 to 22 carbon atoms, a cycloalkyl group having 5 to 22 carbon atoms, an aralkyl group having 7 to 22 carbon atoms, or a cycloalkenyl group having 5 to 22 carbon atoms, each of which groups may be substituted with one or more substituents selected from a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, an acyloxy group, a sulfamoyl group, a carbamoyl group, an acylamino group, a diacylamino group, a ureido group, an N-alkylanilino group, an N-acylanilino group, a hydroxy group, and a mercapto group.

3. A color photographic light-sensitive element as in claim 1, wherein $R_2$ represents an alkyl group having 1 to 32 carbon atoms, an alkenyl group having 2 to 32 carbon atoms, a cycloalkyl group having 5 to 32 carbon atoms, an aralkyl group having 7 to 32 carbon atoms, or a cycloalkenyl group having 5 to 32 carbon atoms, each of which groups may be substituted with one or more substituents selected from a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, an acyloxy group, a sulfamoyl group, a carbamoyl group, an acylamino group, a diacylamino group, a ureido group, an N-alkylanilino group, an N-acylanilino group, a hydroxy group, and a mercapto group.

4. A color photographic light-sensitive element as in claim 1, wherein $R_2$ represents an aryl group which may be substituted with one or more substituents selected from a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, an acyloxy group, a sulfamoyl group, a carbamoyl group, an acylamino group, a diacylamino group, a ureido group, an N-alkylanilino group, an N-acylanilino group, a hydroxy group, and a mercapto group.

5. A color photographic light-sensitive element as in claim 1, wherein $R_2$ represents a 5-membered or 6-membered heterocyclic ring or condensed heterocyclic ring group containing at least one hetero atom selected from a nitrogen atom, an oxygen atom, and a sulfur atom, which ring may be substituted with one or more substituents selected from a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, an acyloxy group, a sulfamoyl group, a carbamoyl group, an acylamino group, a diacylamino group, a ureido group, an N-alkylanilino group, an N-acylanilino group, a hydroxy group, and a mercapto group.

6. A color photographic light-sensitive element as in claim 1, wherein X represents a halogen atom, or an alkoxy group having from 1 to 22 carbon atoms which may be substituted with one or more substituents selected from a halogen atom, a nitro group, a cyano group, an alkoxy group, an aryloxy group, an alkylcarbonyl group, an alkoxycarbonyl group, an acylamine group, a sulfonamido group, a hydroxy group, and a mercapto group.

7. A color photographic light-sensitive element as in claim 1, wherein Z represents hydrogen.

8. A color photographic light-sensitive element as in claim 1, wherein Z represents a coupling-off group.

9. A color photographic light-sensitive element as in claim 8, wherein Z represents hydrogen, a thiocyano group, an acyloxy group, an aryloxy group, an alkoxy group, a halogen atom, an arylazo group, a benzotriazolyl group, a naphthotriazolyl group, an alkylthio group, an arylthio group, a heterocyclic thio group, an aralkoxycarbonyloxy group, an alkoxycarbonyloxy group, an aryloxycarbonyloxy group, a cycloalkylthio group, a cycloalkoxy group, an imido group, an imidazolyl group, a pyrazolyl group, a triazolyl group, an acylamino group, a sulfonamido group or a cycloamino group.

10. A color photographic light-sensitive element as in claim 1, wherein Ar represents an aryl group selected from a phenyl group or a phenyl group substituted with one or more substituents selected from the group consisting of a halogen atom, a cyano group, an alkyl group, an alkoxy group, an acylamino group, a sulfamoyl group, a sulfonamido group, a carbamoyl group, an alkoxycarbonyl group, an alkylsulfonyl group, an alkylthio group, a nitro group and a trifluoromethyl group.

11. A color photographic light-sensitive element as in claim 1, wherein Ar represents an aryl group selected from a phenyl group, a 2-chlorophenyl group, a 4-chlorophenyl group, a 2,5-dichlorophenyl group, a 2,6-dichlorophenyl group, a 2,4,6-trichlorophenyl group, a 2-bromophenyl group, a 3,5-dibromophenyl group, a 2-cyanophenyl group, a 2,6-dichloro-4-cyanophenyl group, a 4-cyanophenyl group, a 4-methylphenyl group, a 2,6-dimethylphenyl group, a 4-butylphenyl group, a 2-trifluoromethylphenyl group, a 2-ethoxyphenyl group, an N-methylbenzamidophenyl group, an N,N-diphenylsulfamoylphenyl group, a phenyl-N-methylsulfonamidophenyl group, a 2,6-dichloro-4-[α-(2,4-di-tert-amylphenoxy)butanamido]phenyl group, a 2,6-dichloro-4-tetradecyloxycarbonylphenyl group, a 2,6-dichloro-4-octadecyloxyphenyl group, a 2,6-dichloro-4-hexadecylthiophenyl group, a 2,6-dichloro-4-octadecylsulfonylphenyl group, a 2,3,4,5,6-pentafluorophenyl group, a 2,3,4,5,6-pentachlorophenyl group, a 2-chloro-5-cyanophenyl group, a 5-chloro-2-methylphenyl group, a 2,6-dichloro-4-methylphenyl group, a 2,4-dichloro-6-methylphenyl group, a 2-chloro-4,6-dimethylphenyl group, and 2,6-dichloro-4-methoxyphenyl group.

12. A color photographic light-sensitive element as in claim 1, wherein said magenta-color-forming coupler is represented by formula (II)

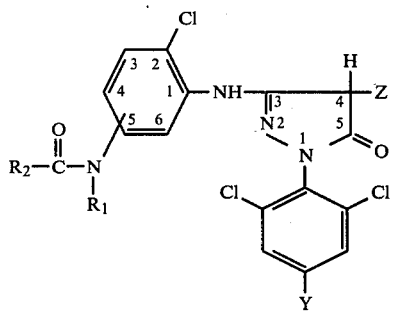

wherein Z, $R_1$, and $R_2$ have the same meanings as defined in claim 1, and Y is selected from the group consisting of hydrogen, a chlorine atom, a cyano group, an acylamino group, a sulfonamino group, an alkoxycarbonyl group, an alkoxycarbonylamino group, an alkylsulfonyl group and an alkylthio group.

13. A color photographic light-sensitive element as in claim 12, wherein $R_1$ and $R_2$ each independently represents an unsubstituted alkyl group, an unsubstituted alkenyl group, or an unsubstituted aralkyl group.

14. A color photographic light-sensitive element as in claim 12, wherein Y represents hydrogen, a chlorine atom, a cyano group, an acylamino group, a sulfonamino group, an alkoxycarbonyl group, an alkoxycarbonylamino group, an alkylsulfonyl group, or an alkylthio group.

15. A color photographic light-sensitive element as in claim 1 or 12, wherein said silver halide emulsion layer is a green-sensitive silver halide emulsion layer.

16. A color photographic light-sensitive element as in claim 1, wherein said silver halide emulsion layer is a green-sensitive silver halide emulsion layer containing said magenta-color-forming coupler represented by formula (I), and said color photographic light-sensitive element further includes a red-sensitive silver halide emulsion layer and a blue-sensitive silver halide emulsion layer.

17. A color photographic light-sensitive element as in claim 1, wherein said silver halide emulsion layer is a green-sensitive silver halide emulsion layer containing said magenta-color-forming coupler represented by formula (I), and said color photographic light-sensitive element additionally includes a red-sensitive silver halide emulsion layer containing a phenolic or naphtholic cyan color-forming coupler, and a blue-sensitive silver halide emulsion layer containing a benzoylacetanilide or pivaloylacetanilide yellow-color-forming coupler.

* * * * *